United States Patent [19]

Saho et al.

[11] Patent Number: 4,996,280

[45] Date of Patent: Feb. 26, 1991

[54] POLYORGANOSILOXANE COMPOUNDS WITH AMINO GROUP

[75] Inventors: Takahiro Saho; Yoshinori Akutsu; Takaharu Nakano; Nobumasa Ohtake, all of Yokohama, Japan

[73] Assignee: Chisso Corporation, Japan

[21] Appl. No.: 387,768

[22] Filed: Aug. 1, 1989

[30] Foreign Application Priority Data

Aug. 1, 1988 [JP] Japan ................................ 63-192317

[51] Int. Cl.$^5$ ............................................. C08G 77/06
[52] U.S. Cl. ........................................ 528/15; 528/42; 528/38; 528/32; 528/31; 556/479; 556/454; 556/462
[58] Field of Search ...................... 528/42, 38, 15, 32, 528/31; 556/479, 454, 462

[56] References Cited

U.S. PATENT DOCUMENTS

| | | | |
|---|---|---|---|
| 3,542,730 | 11/1970 | Papetti et al. | 528/15 |
| 4,658,049 | 4/1987 | Nakano et al. | 556/437 |
| 4,771,119 | 9/1988 | Wrobel | 556/479 |

*Primary Examiner*—Melvyn I. Marquis
*Assistant Examiner*—Karen A. Hellender
*Attorney, Agent, or Firm*—Leydig, Voit & Mayer

[57] ABSTRACT

A polyorganosiloxane compound which has a fluorine-containing group at its one terminal and an aminopropyl group at its other terminal.

The polyorganosiloxane compound can provide various improved properties as well as new properties to synthetic resins by a chemical connection to the synthetic resins with a functional group or groups reactive with the amino group at the other terminal thereof.

10 Claims, No Drawings

POLYORGANOSILOXANE COMPOUNDS WITH AMINO GROUP

BACKGROUND OF THE INVENTION

1. Field of the Invention

The present invention relates to a novel polyorganosiloxane compound with an amino group suitable for modifying synthetic resins.

2. Description of Related Art

Heretofore, silicone resins have been employed for providing synthetic resin molded products with various characteristics such as surface properties, as for example, water repellency, mold releasability and antifouling properties inherent in siloxane compounds as well as thermal resistance. These silicone resins are mainly composed of linear polysiloxane compounds. The linear polysiloxane compounds are physically blended if they do not possess a group or groups reactive with the resins whereas they are chemically introduced into the resins if they possess a group or groups reactive therewith.

Increasing attention has recently been paid to polysiloxane compounds for use as raw materials of graft polymers for modifying synthetic resins. As such polysiloxane compounds have been employed mainly in so-called "polysiloxane compounds modified at one terminal" in which a reactive group resides at only one of their terminals and a trimethylsiloxy group resides at the other terminal.

When the polysiloxane compounds are used with the attempt to improve characteristics of synthetic resins, improvements in characteristics of the synthetic resins rely primarily upon functions inherent in the polysiloxane compounds in order to satisfy recent demands for higher functional characteristics. Therefore, it poses the difficulties that insufficient improvements have been achieved or a large quantity of the polysiloxanes added to achieve characteristics sought adversely affect other characteristics.

When there is used a polysiloxane compound wherein both its terminals are provided with the same substituents which are not reactive with the objective synthetic resin, i.e., a so-called "polysiloxane compound modified at both terminals", it suffers the disadvantages that an amount of the polysiloxane compound to be added cannot be increased on account of bleeding and fluctuations in characteristics which may occur to a remarkably large extent as time elapses, whereby the expected characteristics cannot be maintained for a long period of time.

On the contrary, when the polysiloxane modified at both terminals is used in which groups or substituents reactive with the synthetic resins are used for their surface modifications, it also poses the difficulty that a large amount of the polysiloxane compound should be added, thereby resulting in a remarkable reduction in other properties. Furthermore, it is difficult to use the polysiloxane compound modified at both terminals as a graft polymer which has recently drawn increasing attention for modifying surfaces of the synthetic resins.

In the polysiloxane compound modified at its one terminal, a group at its one terminal which is not reactive with the synthetic resins is generally constituted by a trimethylsiloxy group, and modifications of characteristics for the synthetic resins are dependent upon the properties inherent in the polysiloxane compound. Therefore, demands for higher functions are not achieved to a sufficient extent or a large amount of the polysiloxane compound should be added in order to satisfy the characteristics sought to be attained, thus adversely affecting other properties.

It is further noted that a dimethylsiloxane alone, in which its terminal is terminated by means of the trimethylsiloxy group, can little improve an oil repellency.

SUMMARY OF THE INVENTION

Therefore, is the object the present invention to provide a novel polyorganosiloxane compound with an amino group, which has a fluoroalkyl group at an α-terminal and an amino group at an ω-terminal, which has a fluoroalkyl group at least at α- and α'-terminals and an amino group at an ω-terminal, and which has a fluoroalkyl group at least at α-, α'-, and α"-terminals and an amino group at an ω-terminal. The polyorganosiloxane compounds can improve the difficulties and problems prevailing in conventional polysiloxane compounds.

In accordance with the present invention, the first feature is directed to a polyorganosiloxane compound represented by the following general formula (I):

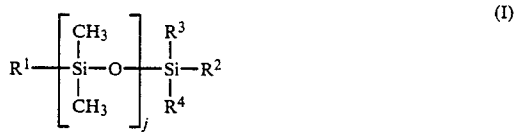

in which j is an integer from 2 to 2,000;

$R^1$ is a pentafluorophenyl group or a linear or branched fluoroalkyl group as represented by the following general formula (II):

$$C_aH_bF_{2a-b+1} \tag{II}$$

wherein a is an integer from 3 to 18; and b is 0 or 2a)
$R^2$ is a substituent as represented by formula (III):

$$-CH_2CH_2CH_2NH_2 \tag{III}$$

; and $R^3$ and $R^4$ are independently each an alkyl group having from 1 to four carbon atoms or a phenyl group. Preferably, the symbols $R^3$ and $R^4$ each independently represents a methyl group.

The second feature of the present invention is directed to a polyorganosiloxane compound in which the substituent represented by the symbol R' is 3,3,3-trifluoropropyl group, tridecafluoro-1,1,2,2-tetrahydrooctyl group or heptadecafluoro-1,1,2,2-tetrahydrodecyl group.

The third feature of the present invention is directed to a polyorganosiloxane compound as represented by the following general formula (VI):

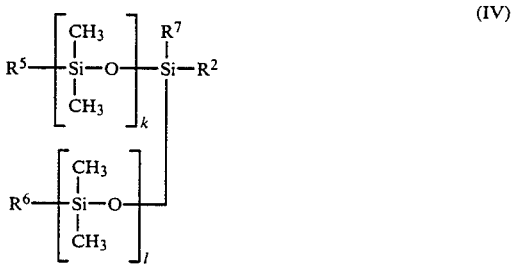

in which k and l are independently each an integer from 2 to 2,000;

$R^5$ and $R^6$ are independently each an alkyl group having from 1 to 4 carbon atoms, pentafluorophenyl group or a linear or branched fluoroalkyl group as represented by the following general formula (II):

$$C_aH_bF_{2a-+1} \qquad (II)$$

wherein a is an integer from 3 to 18; and b is 0 or 2a), provided, however, that at least one of R" and $R^6$ is the pentafluorophenyl group or the fluroalkyl group; $R^2$ is a substituent as represented by formula (III):

$$-CH_2CH_2CH_2NH_2 \qquad (III)$$

; and $R^7$ is an alkyl group having 1 to 4 carbon atoms or a phenyl group.

The fourth feature of the present invention is directed to a polyorganosiloxane compound in which the substituents represented by the symbols $R^5$ and $R^6$ in the general formula (IV) in the above third feature thereof are independently each an alkyl group having 1 to four carbon atoms, 3,3,3-trifluoropropyl group, tridecafluoro1,1,2,2-tetrahydrooctyl group or heptadecafluoro-1,1,2,2-tetrahydrodecyl group, provided, however, that at least and $R^5$ and $R^6$ is the fluorine-containing group. Preferably, the symbol $R^7$ represents a methyl group.

In accordance with the Present invention, the fifth feature is directed to a polyorganosiloxane compound as represented by the following general formula (V):

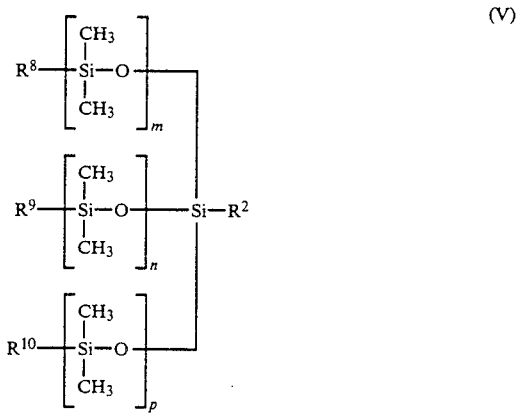

in which m, n and p are independently each an integer from 2 to 2,000;

$R^8$, $R^9$ and $R^{10}$ and are independently each an alkyl group having from 1 to 4 carbon atoms, pentafluorophenyl group or a linear or branched fluoroalkyl group as represented by the following general formula (II):

$$C_aH_bF_{2a-b+1} \qquad (II)$$

wherein a is an integer from 3 to 18; and b is 0 or 2a, provided, however, that at least one of $R^8$, $R^9$ and $R^{10}$ is the pentafluorophenyl group or the fluroalkyl group; and $R^2$ is a substituent as represented by formula (III):

$$-CH_2CH_2CH_2HN_2$$

The sixth feature of the present invention is directed to a polyorganosiloxane compound in which the substituents as represented by the reference symbols $R^8$, $R^9$ and $R^{10}$ of the general formula (V) in the fifth feature above are independently each an alkyl group having from 1 to four carbon atoms, 3,3,3-trifluoropropyl, tridecafluoro-1,1,2,2-tetrahydrooctyl group or heptadecafluoro-1,1,2,2-tetrahydrodecyl group and at least one of $R^8$, $R^9$ and $R^{10}$ is the fluorine-containing substituent selected from the above substituents. Alternatively, the substituents as represented by the reference symbol $R^8$, $R^9$ and $R^{10}$ are each 3,3,3-trifluoropropyl, tridecafluoro-1,1,2,2-tetrahydrooctyl group or heptadecafluoro-1,1,2,2-tetrahydrodecyl group.

DESCRIPTION OF THE PREFERRED EMBODIMENTS

The polyorganosiloxane compound according to the present invention has an amino group at its one terminal and a fluorine-containing substituent at the other terminal as is apparent from the general formulas (I), (IV) and (V) of the first, third and fifth features, respectively.

This can be applied to the polyorganosiloxane having a larger molecular weight in which the reference symbol in the general formula (I), k and l in the general formula (IV), as well as m, n and p in the general formula (V) become larger.

The polyorganosiloxane compounds according to a preferable feature of the present invention are further characterized by a degree of polydispersion, i.e., a ratio of a weight-average molecular weight to a number-average molecular weight, Mw/Mn, in the range from 1.1 to 1.2. In other words, they are said to be a polymer in which a distribution of its molecular weight is highly controlled.

As is apparent from the general formulas (I), (IV) and (V), the respective reference symbols j, k, l, m, n and p each represents the number of dimethylsiloxane units of the linear polydimethylsiloxane moiety, each of the reference symbols is in the range from 2 to 2,000 in order to ensure a manifestation of functional characteristics inherent in the polydimethylsiloxane compound when introduced into the synthetic resins as well as to facilitate an introduction thereof into the synthetic resin and to enable a ready synthesis. Each of the reference symbols k, l, m, n and is preferably below approximately 700 although preferred conditions for introduction of the polyorganosiloxane compounds according to the present invention into the synthetic resins may vary with the kind of synthetic resins, characteristics of the polymers and functions required for the synthetic resins.

In the general formula (II) in the first, third and fifth features according to the present invention the flurooalkyl group represented by the general formula:

$$C_aH_bF_{2a-b+1}$$

is such that the symbol a ranges generally from 3 to 18, preferably from 3 to 10, more preferably from 4 to 6. This range is preferred in terms of ready availability of raw materials, an ease of synthesis, and an effective manifestation of functions inherent in the fluoroalkyl group, such as water or oil repellency, antifouling properties, mold releasability, non-adhesion, low frictional properties, snow resistance and the like.

Although the polyorganosiloxane compounds according to the present invention, having two or three siloxane chains based on the amino-containing substituent, as well as one siloxane chain based thereon, are shown in the general formulas (IV), (V), and (I) in the respective third, fifth and first features of the present invention, they may be chosen depending upon the kinds of synthetic resins and functional characteristics to be added by introduction of the polyorganosiloxane compounds. When the polyorganosiloxane compounds having two or three siloxane chains based thereon are to be used as graft polymers for modifying the synthetic resins, it is preferred that the siloxane chains have the same length although the polyorganosiloxane compound with the plural siloxane chains of different lengths may be used in accordance with usage of the synthetic resins to which it is added. It is further to be noted that the substituents as represented by the symbols $R^5$ and $R^6$ of the general formula (IV) in the third feature and the symbols $R^8$, $R^9$ and $R^{10}$ of the general formula (V) in the fifth feature according to the present invention, which are different from each other, may be introduced into the plural siloxane chains of the polyorganosiloxane compound. However, as manufacture of the polyorganosiloxane compounds with the plural siloxane chains having different chain length and substituents is made complicated and conditions for synthesis become more difficult, these compounds are not preferred unless a unique function is required to be added to the synthetic resin or a more sensitive control over functional characteristics to be added should be made. It is preferred that the siloxane chains are usually the same in chain length and substituents as each other.

The polyorganosiloxane compound as represented by the general formula (I) in the first feature, the general formula (IV) in the third feature, and the general formula (V) in the fifth feature of the present invention may be used as useful modifiers for functions of the synthetic resins, such as polyamides, polyimides, polyurethanes, epoxy resins or the like, by reaction with their group reactive with the amino group at one terminal of the polyorganosiloxane compound. This chemical introduction of the polyorganosiloxane compound according to the present invention can provide the synthetic resins with superior modifications in their surface characteristics.

Preparation procedures of the polyorganosiloxane compounds represented by the general formulas (I), (IV) and (V) are shown below referring to concrete examples:

(1) The polyorganosiloxane compound having ne siloxane chain based on the amino-containing substituent:
The reaction scheme may be described as follows:

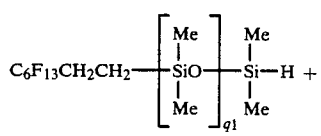

(VI)

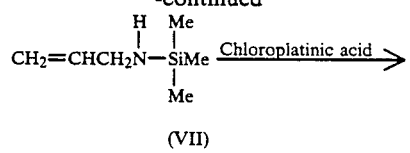

(VII)

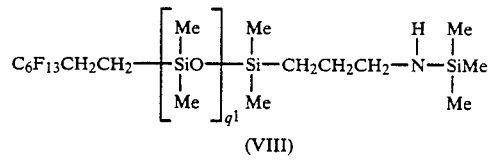

(VIII)

↓ Desilylation

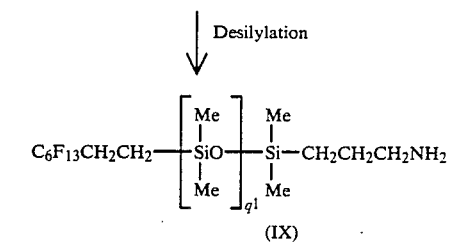

(IX)

(wherein Me is methyl and $q^1$ is an integer from 2 to 2,000).

Using (tridecafluoro-1,1,2,2-tetrahydrooctyl)dimethylsilanol as an initiator, hexamethylcyclotrisiloxane is first subjected to anionic polymerization in the presence of a 0.05-50 mol % lithium catalyst in a polar solvent having no active hydrogen. Dimethylchlorosilane is then added to terminate the polymerization, thereby yielding a dimethylsiloxane compound (VI) having a tridecafluoro-1,1,2,2-tetrahydrooctyl group at an α-terminal and a hydrosilyl group at an ω-terminal.

The dimethylsiloxane compound (VI) is then hydrosilylated with 3-(N-trimethylsilyl)amino-1-propene (VII) in the presence of a catalyst to give a siloxane compound (VIII). Thereafter, the trimethylsilyl group of the siloxane compound (VIII) is removed by means of an alcohol such as methanol or ethanol yielding the object compound, an organosiloxane compound (IX).

(2) The polyorganosiloxane compound having two siloxane chains based on the amino-containing substituent:

The reaction scheme may be described as follows:

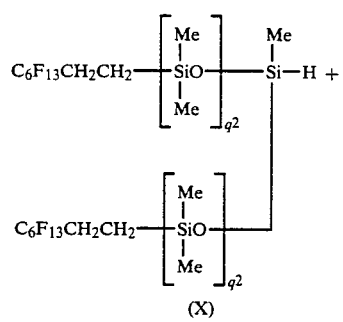

(X)

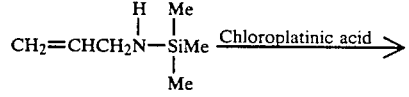

(VII)

-continued

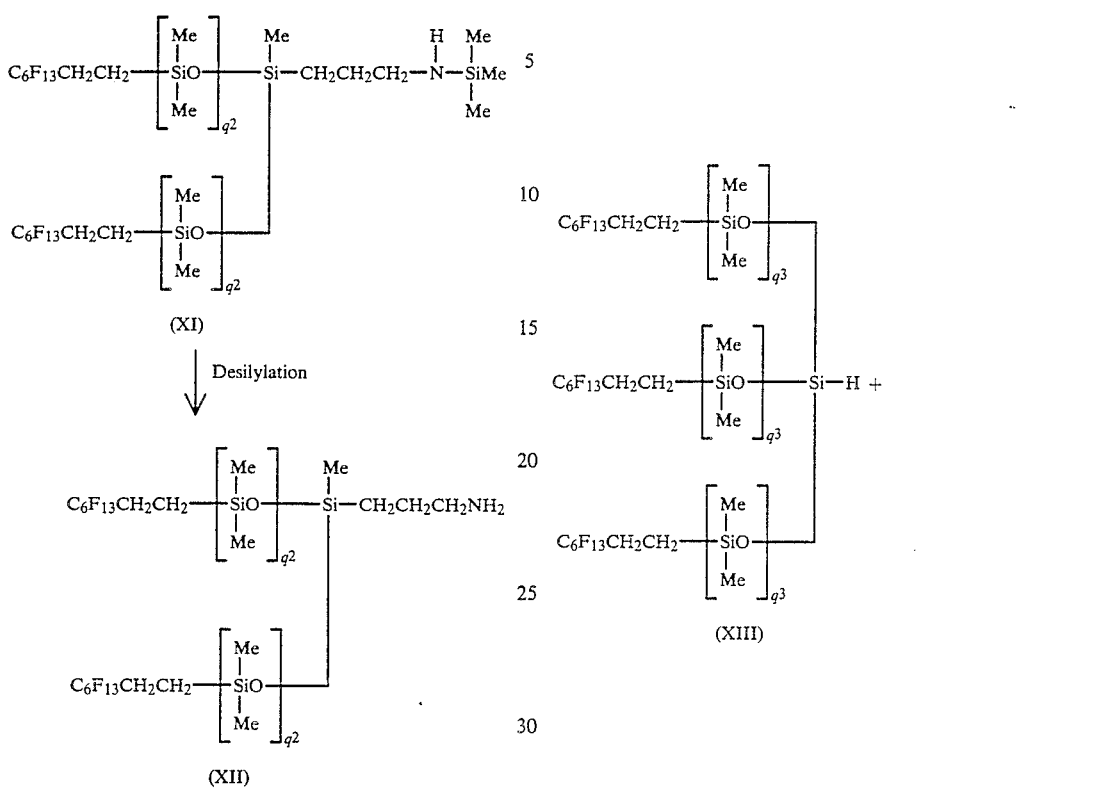

wherein Me is methyl and $q^2$ is an integer from 2 to 2,000).

Using (tridecafluoro-1,1,2,2-tetrahydrooctyl)dimethylsilanol as an initiator, hexamethylcyclotrisiloxane is first subjected to anionic polymerization in the presence of a 0.05–50 mol % lithium catalyst in a polar solvent having no active hydrogen. Methyldichlorosilane is then added to terminate the polymerization, thereby yielding a dimethylsiloxane compound (X) having a tridecafluoro-1,1,2,2-tetrahydrooctyl group at α- and α'-terminal positions and a hydrosilyl group at an ω-terminal position.

The dimethylsiloxane compound (X) is then hydrosilylated with 3-(N-trimethylsilyl)amino-1-propene (VII) in the presence of a catalyst to give a siloxane compound (XI). Thereafter, the trimethylsilyl group of the siloxane compound (XI) is removed by means of a dilute hydrochloric acid or an alcohol such as methanol or ethanol yielding the object compound, an organosiloxane compound (XII). compound (XII).

(3) The polyorganosiloxane compound having three siloxane chains based on the amino-containing substituent:

The reaction scheme may be described as follows:

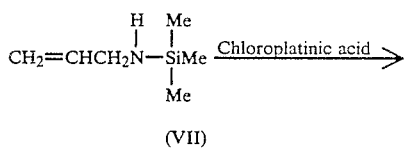

(VII)

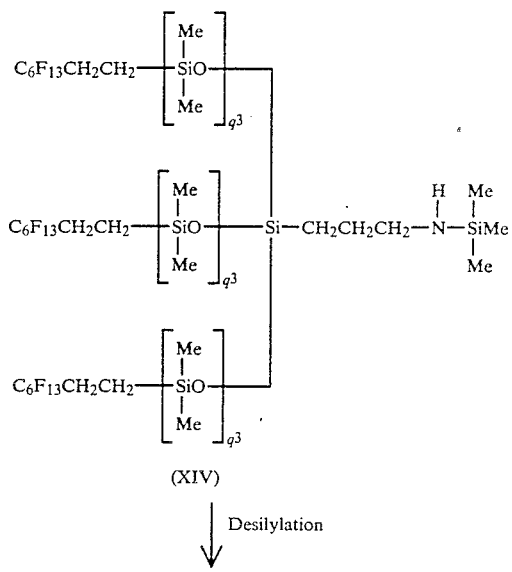

(XIV)

| Desilylation
↓

-continued

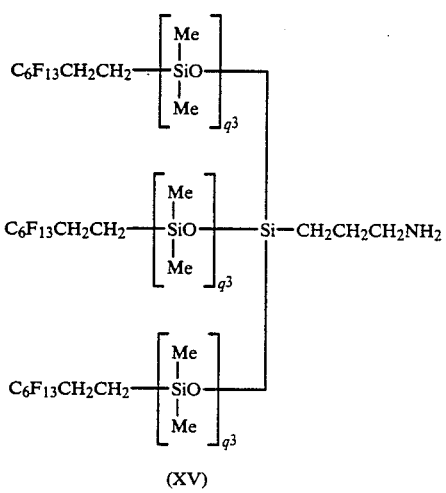

(wherein Me is methyl and $q^3$ is an integer from 2 to 2,000.

Using (tridecafluoro-1,1,2,2-tetrahydrooctyl)dimethylsilanol as an initiator, hexamethylcyclotrisiloxane is first subjected to anionic polymerization in the presence of a 0.05–50 mol % lithium catalyst in a polar solvent having no active hydrogen. Trichlorosilane is then added to terminate the polymerization, thereby yielding a dimethylsiloxane compound (XIII) having a tridecafluoro1,1,2,2-tetrahydrooctyl group at $\alpha$-, $\alpha'$- and $\alpha''$-terminal positions and a hydrosilyl group at an $\omega$-terminal position.

The dimethylsiloxane compound (XIII) is then hydrosilylated with 3-(N-trimethylsilyl)amino-1-propene (VII) in the presence of a catalyst to give a siloxane compound (XIV). Thereafter, the trimethylsilyl group of the siloxane compound (XIV) is removed by means of a dilute hydrochloric acid or an alcohol such as methanol or ethanol yielding the object compound, an organosiloxane compound (XV).

In preparing the polyorganosiloxane compounds according to the present invention having one, two or three siloxane chains based on the amino-containing substituent, a control over molecular weights and a distribution of the molecular weights is made by the siloxane compounds represented by the formulas (VI), (X), and (XIII), respectively. The siloxane compounds with the objective molecular weights with a number-average molecular weight of approximately 150,000 or lower (2,000 or lower of siloxane units) per siloxane chain may be synthesized without difficulty by changing a ratio of an initiator, such as a trialkylsilanol, i.e.. (tridecafluoro1,1,2,2-tetrahydrooctyl)dimethylsilanol, to hexamethylcyclotrisiloxane. The siloxane compounds having a molecular weight larger than the above molecular weight may be prepared by changing polymerization conditions.

The trialkylsilanol to be used as an initiator for the anionic polymerization may be readily available by hydrolyzing a trialkylchlorosilane having the objective alkyl group. The trialkylchlorosilane may be represented by the following general formula:

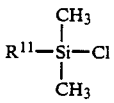

wherein
$R^{11}$ is pentafluorophenyl group or a linear or branched fluoroalkyl alkyl group as represented by the following general formula (II):

$$C_aH_bF_{2a-b+1} \qquad (II)$$

where a is an integer from 3 to 18; and b is 0 or an integer of 2a;
when the organosiloxane compound as represented by the formula (I) above is prepared, or an alkyl group having 1 to 4 carbon atoms, a phenyl group, pentafluorophenyl group or a linear or branched fluoroalkyl group as represented by the general formula (II) above when the organosiloxane compound as represented by the general formula (IV) or (VII) above is prepared.

The trialkylchlorosilane as represented by the general formula above may include, for example, trimethylchlorosilane, ethyldimethylchlorosilane, n-butyldimethylchlorosilane. t-butyldimethylchlorosilane, isopropyldimethylchlorosilane, n-propyldimethylchlorosilane, pentafluorophenyldimethylchlorosilane, 3,3,3-trifluoropropyldimethylchlorosilane. (tridecafluoro-1,1,2,2-tetrahydrooctyl)dimethylchlorosilane, (heptadecafluoro-1,1,2,2-tetrahydrodecyl)dimethylchlorosilane or the like.

The lithium catalyst to be used for synthesis of the compound according to the present invention may include, for example, a metal lithium, butyl lithium, lithium hydroxide or a lithium trialkylsilanolate as represented by following general formula:

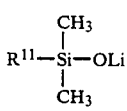

where $R^{11}$ has the same meaning as above.
The lithium catalyst may be used singly or in combination thereof. It is further to be noted that, for example, a sodium catalyst, potassium catalyst or other alkali metal catalyst may be employed, however, it is not preferred because a yield of the siloxane compound may be reduced.

The amount of the catalyst for the anionic polymerization may be in the range generally from 0.05 mol% to 50 mol%, preferably from 0.05 mol% to 10 mol%, with respect to the amount of the trialkylsilanol as a polymerization initiator. If the catalyst is used in an amount below the lower limit, a polymerization speed becomes too slow to be practical. It is preferred to use the catalyst in the amount up to 50 mol%, generally up to 10 mol%, if metering would become inaccurate on account of too small an amount in the case where a synthesis scale is too small or a polymer with a high molecular weight is synthesized. Even if the catalyst is used in amounts from 50 mol% to 100 mol%, synthesis proceeds without difficulty, however, the use of the catalyst in such a large amount is not preferred because security may be impaired, production efficiency may be reduced, and production cost may be raised due to the use of a dangerous catalyst, unless special circumstances arise.

The polar solvent having no active hydrogen to be used for synthesis of the polyorganosiloxane compounds may include, for example, tetrahydrofuran, 1,4-dioxane, ethyleneglycol dimethylether, diethyleneglycol dimethylether, dimethylformamide, dimethylsulfoxide or the like. Preferred is tetrahydrofuran although the solvent may be used in combination thereof. A solvent with an active hydrogen interferes with the reaction and a non-polar solvent causes the reaction to proceed slowly so that these solvents cannot be used.

Generally, reaction temperatures may be in the range generally from 0° C. to 50° C., preferably from 15° C. to 25° C. If the reaction temperature becomes too low, polymerization speed becomes too slow to be practical, while a reaction temperature above the upper limit is not preferred because it causes a polysiloxane compound to have too a molecular weight distribution.

Reaction time may vary with reaction temperatures and it is preferred to determine the reaction time so as to suspend the reaction at the time when the hexamethyl cyclotrisiloxane is consumed by approximately 95%. For example, a period of time ranging from 10 to 20 hours is appropriate in the case of reaction temperatures ranging from 15° C. to 20° C. A reaction time longer than necessary is not preferred because it broadens a molecular weight distribution too much.

3-(N-Trimethylsilyl)amino-1-propene as represented by formula (VII) above, in which the hydroxyl group at its terminal of 3-amino-1-propene is protected with a trimethylsilyl group, may be readily prepared by reacting 3-amino-1-propene with hexamethyldisilazane in the presence of trimethylchlorosilane.

For the hydrosilylation, the catalyst to be used may be a complex compound of a metallic element of Group VIII of the Periodic Table, including preferably chloroplatinic acid or a complex of platinum or rhodium with an olefin. An amount of chloroplatinic acid as a catalyst may be in the range preferably from $1 \times 10^{-3}$ to $1 \times 10^{-6}$ mol per mol of the siloxane compound as represented by the general formula (VI), (X) or (XIII). If the catalyst is used above the upper limit, it may incur the increasing possibility of breaking the siloxane chain and raise the cost of production due to the use of the catalyst in too great an amount. If the amount of the catalyst is below the lower limit, the reaction likely undergoes influences from a minute amount of moisture or substances detrimental to the reaction so that the reaction may not proceed in a smooth manner.

A reaction temperature may be in the range preferably from 50° C. to 150° C., more preferably from 80° C. to 120° C. The reaction temperature below the lower limit may pose problems. The reaction does not proceed smoothly or a reaction period of time becomes too long. If the reaction temperature would exceed the upper limit, it is not preferred since a siloxane chain may be broken or a side reaction may arise upon removal of the trimethylsilyl group from the protective site of an olefin such as 3-(N-trimethysilyl)amino-1-propene (VII).

In a similar manner as has been described above, there may be prepared organosiloxane compounds according to the present invention, which have a fluorine-containing group at its $\alpha'$-position and an amino group at its $\omega$-position, which has a fluorine-containing group at least at its and $\alpha$-, $\alpha'$- and $\alpha''$-positions and an amino group at its $\omega$-position or which has a fluorine-containing group at least at its $\alpha$-, $\alpha'$- and $\alpha''$-positions and an amino group at its $\omega$-position.

The present invention will be described in more detail by way of examples.

REFERENCE EXAMPLE 1

Preparation of 1-(tridecafluoro-1,1,2,2-tetrahydrooctyl)-9-hydrodecamethyl pentasiloxane A 1-liter three-necked round flask with a stirrer and a cooler was charged with 100 ml of previously dried tetrahydrofuran, 100.0 g (0.238 mol) of (tridecafluoro-1,1,2,2-tetrahydrooctyl)dimethylsilanol, and 52.9 g (0.238 mol) of hexamethylcyclotrisiloxane in a nitrogen stream, and 0.79 ml of a hexane solution of butyl lithium (1.5 mol/liter) was added to the mixture. The polymerization was then carried out at 20° C. for 10 hours.

To the reaction mixture were then added 24.7 g (0.261 mol) of dimethylchlorosilane and 27 g of triethyl amine, and the mixture was stirred for 1 hour to suspend the polymerization. The product was then transferred to a separatory funnel and the salt produced was removed by washing with water. The product was then dried over anhydrous sodium sulfate.

A low-boiling fraction of the reaction product was removed at 100° C./100 mmHg over a period of 2 hours and the object product was left as a still residue in a substantially quantitative yield. The resulting siloxane compound was measured by $^1$H-NMR spectrum, IR spectrum, and gel permeation chromatography (GPC) and the analysis results and Si—H group quantitation data are as shown below. The resulting product was identified as having the following formula:

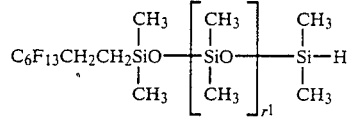

$^1$H-NMR (CDCl$_3$): δ ppm
0.18 (Si (C$\underline{H}_3$)$_2$, s , 30H)
0.53~1.80 (SiC$\underline{H}_2$C$\underline{H}_2$, broad, 4H)
4.55 (Si—H, m, 1H)
IR (KBr):
2970cm$^{-1}$: (C—H)
2250cm$^{-1}$: (Si—H)
1260cm$^{-1}$: (Si—CH$_3$)
1250–1150cm$^{-1}$: (CF$_2$, CF$_3$)
1120–1050cm$^{-1}$: (Si—O)
GPC (toluene), molecular weight converted into polystyrene
number-average molecular weight (Mn): 850
weight-average molecular weight (Mw): 930
polydisperssion degree (Mw/Mn): 1.1
(calculated molecular weight,: 702)
Quantitation Data of Si—H group:
H (ppm): 1442(ppm)
Molecular weight calculated from H(ppm): 693
r$^1$ in the present example and r$^2$–r$^7$ in subsequent examples may be calculated based on the following general formula and equation.

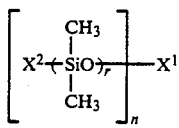

where
$X^2$ = Substituent containing an amino group
$X^1$ = Substituent containing OH
r = Number of units
n = 1 to 3 (n = 1 in page 24)

$$r = [\{(a-b)/n\} - c]/d$$

where
a = Calculated molecular weight from quantitation data
b = Calculated molecular weight of $X^2$
c = Calculated molecular weight of $X^1$
d = Calculated molecular weight of $-Si(CH_3)_2-$

EXAMPLE 1

Preparation of 1-(tridecafluoro-1,1,2,2-tetrahydrooctyl)-9-(3-aminopropyl)decamethylpentasiloxane A 1-liater three-necked round flask with a stirrer and a cooler was charged with 34.7 g of 1-(tridecafluoro1,1,2,2-tetrahydrooctyl)-9-hydrodecamethylpentasiloxane prepared in Reference Example 1 above and heated to 110° C. After $5.2 \times 10^{-4}$ g ($1.0 \times 10^{-6}$ mol) of chloroplatinic acid was added, 7.1 g (0.055 mol) of 3-(N-trimethylsilylamino)propene was added dropwise. After completion of dropwise addition, the mixture was maintained at the reaction temperature of 110° C. for 5 hours and then subjected to a reaction for removing a trimethylsilyl group using 100 g of methanol.

A low-boiling fraction of the reaction product was removed at 100° C./100 mmHg over a period of 2 hours and the object product was left as a still residue in a substantially quantitative yield. The resulting siloxane compound was measured by $^1$H-NMR spectrum, IR spectrum, gel permeation chromatography (GPC) and viscosity, and the analysis results and amino group quantitation data are as shown below. The resulting product was identified as having the following formula:

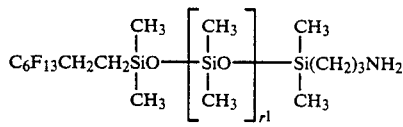

$^1$H-NMR (CDCl$_3$): δ ppm
0.18: (Si(CH$_3$)$_2$, s, 30H)
0.53—1.80: (SiCH$_2$CH$_2$—, broad 8H)
1.70: (—NH$_2$, s, 2H)
2 58: (—CH$_2$N=, t, 2H)
IR (KBr):
3400~3250cm$^{-1}$: (—NH$_2$)
2970cm$^{-1}$: (C—H)
1260cm$^{-1}$: (Si—CH$_3$)
1250-1150cm$^{-1}$: (CF$_2$, CF$_3$)
1120-1050cm$^{-1}$: (Si—O)
GPC (toluene), molecular weight converted into polystyrene
number-average molecular weight (Mn): 875
weight-average molecular weight (Mw): 980
polydispersion degree (Mw/Mn): 1.1
(calculated molecular weight,: 759)
Quantitation Data of amino group:
amine equivalent: 756
Viscosity (25° C.): 11 centipoises

REFERENCE EXAMPLE 2

Preparation of dimethylsiloxane compound with a tridecafluoro-1,1,2,2-tetrahydrooctyl group at its α-position and a hydrosilyl group at its ω-position A 5-liter three-necked round flask with a stirrer and a cooler was charged with 2,000 ml of previously dried tetrahydrofuran, 12.0 g (0.0285 mol) of (tridecafluoro-1,1,2,2-tetrahydrooctyl)dimethylsilanol, and 1,981.1 g (8.90 mol) of hexamethylcyclotrisiloxane in a N$_2$ stream. To this mixture was added 0.095 ml of a hexane solution of butyl lithium (1.5 mol/liter), and the mixture was subjected to polymerization at 20° C. for 20 hours.

To this reaction mixture were then added 2.97 g (0.031 mol) of dimethylchlorosilane and 3.17 g of triethylamine, and the mixture was stirred for 1 hour to suspend the polymerization. After the reaction mixture was transferred to a separatory funnel and the salt produced was removed by washing with water, the reaction product was dried over anhydrous sodium sulfate.

A low-boiling fraction of the reaction product was removed at 100° C./10 mmHg over a period of 2 hours and the object product was left as a still residue in a substantially quantitative yield. The resulting siloxane compound was measured by IR spectrum, gel permeation chromatography (GPC) and viscosity, and the analysis results and Si—H group quantitation data are as shown below.
IR (KBr):
2970cm$^{-1}$: (C—H)
2250cm$^{-1}$: (Si—H)
1260cm$^{-1}$: (Si—CH$_3$)
1250-1150cm$^{-1}$: (CF$_2$, CF$_3$)
1120-1050cm$^{-1}$: (Si—O)
GPC (toluene), molecular weight converted into polystyrene
number-average molecular weight (Mn): 63,410
weight-average molecular weight (Mw): 75,930
polydispersion degree (MW/Mn): 1 2
Quantitation Data of Si—H group:
H (ppm): 15.1:
calculated molecular weight
from H (ppm): 66,225
Viscosity (25° C.): 3,538 centipoises

EXAMPLE 2

Preparation of dimethylsiloxane compound with a tridecafluoro-1,1,2,2-tetrahydrooctyI group at its α-position and a 3-aminopropyl group at its ω-position A 3-liter three-necked round flask with a stirrer and a cooler was charged with 662.2 g of the siloxane compound prepared in Reference Example 2 and 500 ml of toluene and heated to 110° C. After addition of $5.2 \times 10^{-4}$ g ($1.0 \times 10^{-6}$ mol) of chloroplatinic acid, 1.42 g (0.011 mol) of 3-(N-trimethylsilylamino)propene was added dropwise. After the completion of dropwise addition, the reaction mixture was maintained at the reaction temperature of 110° C. for 20 hours and subjected to a reaction for removing its trimethylsilyl group using 300 g of methanol.

A low-boiling fraction of the reaction product was removed at 100° C./10 mmHg over a period of 2 hours and the object product was left as a still residue in a substantially quantitative yield. The resulting siloxane compound was measured by IR spectrum, gel permeation chromatography (GPC) and viscosity, and the analysis results and OH group quantitation data are as shown below. IR (KBr):

3400–3250cm$^{-1}$: (—NH$_2$)
2970cm$^{-1}$: (C—H)
1260cm$^{-1}$: (Si—CH$_3$)
1250–1150cm$^{-1}$: (CF$_2$, CF$_3$)
1120–1050cm$^{-1}$: (Si—O)

GPC (toluene), molecular weight converted into polystyrene
  number-average molecular weight (Mn): 64,200
  weight-average molecular weight (Mw): 76,270
  polydispersion degree (Mw/Mn): 1.2

Quantitation Data of amino group: amine equivalent: 66,800

Viscosity (25° C.): 3,520 centipoises

REFERENCE EXAMPLE 3

Preparation of dimethylsiloxane compound with a heptadecafluoro-1,1,2,2-tetrahydrodecyl group at its α-position and a hydrosilyl group at its ω-position A 5-liter three-necked round flask with a stirrer and a cooler was charged with 2,000 ml of previously dried tetrahydrofuran, 100.0 g (0.1915 mol) of (heptadecafluoro-1,1,2,2-tetrahydrodecyl)dimethylsilanol, and 1,803.6 g (8.10 mol) of hexamethylcyclotrisiloxane in a N$_2$ stream. After 0.64 ml of a hexane solution of butyl lithium (1.5 mol/liter) was added, the mixture was polymerized at 20° C. for 15 hours.

To this reaction mixture were added 19.9 g (0.211 mol) of dimethylchlorosilane and 21.4 g of triethylamine, and the resulting mixture was stirred for 1 hour to suspend the polymerization. The reaction mixture was then transferred to a seParatory funnel and the salt produced was removed by washing with water. Thereafter, the reaction product was dried over anhydrous sodium sulfate.

A low-boiling fraction of the reaction product was removed at 100° C./10 mmHg over a period of 2 hours and the object product was left as a still residue in a substantially quantitative yield. The resulting siloxane compound was measured by IR spectrum, gel permeation chromatography (GPC) and viscosity, and the analysis results and Si—H group quantitation data are as shown below IR (KBr):
2970cm$^{-1}$: (C—H)
2250cm$^{-1}$: (Si—H)
1260cm$^{-1}$: (Si—CH$_3$)
1250–1150cm$^{-1}$: (CF$_2$, CF$_3$)
1120–1050cm$^{-1}$: (Si—O)

GPC (toluene), molecular weight converted into polystyrene
  number-average molecular weight (Mn): 11,710
  weight-average molecular weight (Mw): 12,896
  polydispersion degree (Mw/Mn): 1.1

Quantitation Data of Si—H group:
H (ppm): 103.3
calculated molecular weight from H (ppm): 9,680
Viscosity (25° C.): 147 centipoises

EXAMPLE 3

Preparation of dimethylsiloxane compound with a heptadecafluoro-1,1,2,2-tetrahydrodecyl group at its α-position and a 3-aminopropyl group at its ω-position A 3-liter three-necked round flask with a stirrer and a cooler was charged with 968.0 g of the siloxane compound prepared in Reference Example 3 and 500 ml of toluene and heated to 110° C. After addition of 5.2×10$^{-4}$ g (1.0×10$^{-6}$ mol) of chloroplatinic acid, 14.2 g (0.11 mol) of 3-(N-trimethylsilylamino)propene was added dropwise. After the completion of dropwise addition, the reaction mixture was maintained at the reaction temperature of 110° C. for 20 hours and subjected to a reaction for removing its trimethylsilyl group using 500 g of methanol.

A low-boiling fraction of the reaction product was removed at 100° C./10 mmHg over a period of 2 hours and the object product was left as a still residue in a substantially quantitative yield. The resulting siloxane compound was measured by IR spectrum, gel permeation chromatography (GPC) and viscosity, and the analysis results and amino group quantitation data are as shown below.

IR (KBr):
3400–3250cm$^{-1}$: (—OH)
2970cm$^{-1}$: (C—H)
1260cm$^{-1}$: (Si—CH$_3$)
1250–1150cm$^{-1}$: (CF$_2$, CF$_3$)
1120–1050cm$^{-1}$: (Si—O)

GPC (toluene), molecular weight converted into polystyrene
  number-average molecular weight (Mn): 11,830
  weight-average molecular weight (Mw): 12,900
  polydispersion degree (Mw/Mn): 1.1
Quantitation Data of amino group:
amine equivalent: 9,930
Viscosity (25° C.): 156 centipoises

REFERENCE EXAMPLE 4

Preparation of dimethylsiloxane compound with a 3,3,3-trifluoropropyl group at its α-position and a hydrosilyl group at its ω-position A 2-liter three-necked round flask with a stirrer and a cooler was charged with 800 ml of previously dried tetrahydrofuran, 10.0 g (0.0581 mol) of (3,3,3-trifluoropropyl)dimethylsilanol, and 567.2 g (2.55 mol) of hexamethylcyclotrisiloxane in a N$_2$ stream. After 0.19 ml of a hexane solution of butyl lithium (1.5 mol/liter) was added, the mixture was polymerized at 20° C. for 15 hours.

To this reaction mixture were added 6.04 g (0.0639 g mol) of dimethylchlorosilane and 6.5 g of triethylamine, and the resulting mixture was stirred for 1 hour to suspend the polymerization. The reaction mixture was then transferred to a separatory funnel and the salt produced was removed by washing with water. Thereafter, the reaction product was dried over anhydrous sodium sulfate.

A low-boiling fraction of the reaction product was removed at 100° C./10 mmHg over a period of 2 hours and the object product was left as a still residue in a substantially quantitative yield. The resulting siloxane compound was measured by IR spectrum, gel permeation chromatography (GPC) and viscosity, and the analysis results and Si—H group quantitation data are as shown below.

IR (KBr):
2970cm$^{-1}$: (C—H)
2250cm$^{-1}$: (Si—H)
1260cm$^{-1}$: (Si—CH$_3$)
1250–1150cm$^{-1}$: (CF$_2$, CF$_3$)
1120–1050cm$^{-1}$: (Si—O)
GPC (toluene), molecular weight converted into polystyrene
number-average molecular weight (Mn): 9,520
weight-average molecular weight (Mw): 10,490
polydispersion degree (Mw/Mn): 1.1
Quantitation Data of Si—H group:
H (ppm): 112.5
calculated molecular weight
from H (ppm): 8,890
Viscosity (25° C.): 116 centipoises

EXAMPLE 4

Preparation of dimethylsiloxane compound with a 3,3,3-trifluoropropyl group at its α-position and a 3-aminopropyl group at its ω-position A 1-liter three-necked round flask with a stirrer and a cooler was charged with 88.9 g of the siloxane compound prepared in Reference Example 4 and 50 ml of toluene and heated to 110° C. After addition of 5.2×10$^{-4}$ g (1.0 ×10$^{-6}$ mol) of chloroplatinic acid, 1.42 g (0.011 mol) of 3-(N-trimethylsilylamino)propene was added dropwise. After the completion of dropwise addition, the reaction mixture was maintained at the reaction temperature of 110° C. for 20 hours and subjected to a reaction for removing its trimethylsilyl group using 300 g of methanol.

A low-boiling fraction of the reaction product was removed at 100° C./10 mmHg over a period of 2 hours and the object product was left as a still residue in a substantially quantitative yield. The resulting siloxane compound was measured by IR spectrum, gel permeation chromatography (GPC) and viscosity, and the analysis results and amino group quantitation data are as shown below.

IR (KBr):
3400–3250cm$^{-1}$: (—NH$_2$)
2970cm$^{-1}$: (C—H)
1260cm$^{-1}$: (Si—CH$_3$)
1250–1150cm$^{-1}$: (CF$_2$, CF$_3$)
1120–1050cm$^{-1}$: (Si—O)
GPC (toluene), molecular weight converted into polystyrene
number-average molecular weight (Mn): 10,050
weight-average molecular weight (Mw): 11,280
polydispersion degree (Mw/Mn): 1.1
Quantitation Data of amino group:
amine equivalent: 9,410
Viscosity (25° C.): 138 centipoises

REFERENCE EXAMPLE 5

Preparation of dimethylsiloxane compound with a pentafluorophenyl group at its α-position and a hydrosilyl group at its ω-position A 1-liter three-necked round flask with a stirrer and a cooler was charged with 100 ml of previously dried tetrahydrofuran, 10.0 g (0.04127 mol) of pentafluorophenyldimethylsilanol, and 194.0 g (0.138 mol) of hexamethylcyclotrisiloxane in a N$_2$ stream. After 0.14 ml of a hexane solution of butyl lithium (1.5 mol/liter) was added, the mixture was Polymerized at 20° C. for 15 hours.

To this reaction mixture were added 4.29 g (0.0454 mol) of dimethylchlorosilane and 4.6 g of triethylamine, and the resulting mixture was stirred for 1 hour to suspend the polymerization. The reaction mixture was then transferred to a separatory funnel and the salt produced was removed by washing with water. Thereafter, the reaction product was dried over anhydrous sodium sulfate.

A low-boiling fraction of the reaction Product was remove at 100° C./10 mmHg over the period of 2 hours and the object product was left as a still residue in a substantially quantitative yield.

The resulting siloxane compound was measured by IR spectrum, gel permeation chromatography (GPC) and viscosity, and the analysis results and Si—H group quantitation data are as shown below.

IR (KBr):
2970cm$^{-1}$: (C—H)
2250cm$^{-1}$: (Si—H)
1260cm$^{-1}$: (Si—CH$_3$)
1120–1050cm$^{-1}$: (Si—O)
GPC (toluene), molecular weight converted into polystyrene
number-average molecular weight (Mn): 5,807
weight-average molecular weight (Mw): 6,370
polydispersion degree (Mw/Mn): 1.1
Quantitation Data of Si—H group:
H (ppm): 203.3
calculated molecular weight
from H (ppm): 4,920
Viscosity (25° C.): 64 centipoises

EXAMPLE 5

Preparation of dimethylsiloxane compound with a pentafluorophenyl group at its α-position and a 3-Aaminopropyl group at its ω-position A 1-liter three-necked round flask with a stirrer and a cooler was charged with 49.2 g of the siloxane compound prepared in Reference Example 5 and 50 ml of toluene and heated to 110 After addition of 5.2×10$^{-4}$ g (1.0 ×10$^{-6}$ mol) of chloroplatinic acid, 1.42 g (0.011 mol) of 3-(N-trimethylsilylamino)propene was dropwise added. After the completion of dropwise addition, the reaction mixture was maintained at the reaction temperature of 110° C. for 20 hours and subjected to a reaction for removing its trimethylsilyl group using 300 g of methanol.

A low-boiling fraction of the reaction product was removed at 100° C./10 mmHg over a period of 2 hours and the object product was left as a still residue in a substantially quantitative yield.

The resulting siloxane compound was measured by IR spectrum, gel permeation chromatography (GPC) and viscosity, and the analysis results and amino group quantitation data are as shown below.

IR (KBr):
3400–3250cm$^{-1}$: (—NH$_2$)
2970cm$^{-1}$: (C—H)
1260cm$^{-1}$: (Si—CH$_3$)
1250–1150cm$^{-1}$: (CF$_2$, CF$_3$)
1120–1050cm$^{-1}$: (Si—O)
GPC (toluene), molecular weight converted into polystyrene number-average molecular weight (Mn): 5,870
weight-average molecular weight (Mw): 6,450
Polydispersion degree (Mw/Mn): 1.1
Quantitation Data of amino group
amino group: 5,020
Viscosity (25° C.): 84 centipoises

REFERENCE EXAMPLE 6

Preparation of dimethylsiloxane compound with a tridecafluoro-1,1,2,2-tetrahydrooctylphenyl group at its α-position and a hydrosilyl group at its ω-position A 5-liter three-necked round flask with a stirrer and a cooler was charged with 1,000 ml of previously dried tetrahydrofuran, 50.0 g (0.119 mol) of (tridecafluoro1,1,2,2-tetrahydrooctyl)dimethylsilanol, and 1,130.2 g (5.08 mol) of hexamethylcyclotrisiloxane in a N₂ stream. After 0.40 ml of a hexane solution of butyl lithium (1.5 mol/liter) was added, the mixture was polymerized at 20° C. for 15 hours.

To this reaction mixture were added 12.35 g (0.1306 mol) of dimethylchlorosilane and 14 g of triethylamine, and the resulting mixture was stirred for 1 hour to suspend the polymerization. The reaction mixture was then transferred to a separatory funnel and the salt produced was removed by washing with water. Thereafter, the reaction product was dried over anhydrous sodium sulfate.

A low-boiling fraction of the reaction product was removed at 100° C./10 mmHg over a period of 2 hours and the object product was left as a still residue in a substantially quantitative yield.

The resulting siloxane compound was measured for IR spectrum, gel permeation chromatography (GPC) and viscosity, and the analysis results and Si—H group quantitation data are as shown below.

IR (KBr):
2970cm⁻¹: (C—H)
2250cm⁻¹: (Si—H)
1260cm⁻¹: (Si—CH₃)
1250-1150cm⁻¹: (CF₂, CF₃)
1120-1050cm⁻¹: (Si—O)
GPC (toluene), molecular weight converted into polystyrene
number-average molecular weight (Mn): 11,910
weight-average molecular weight (Mw): 12,850
polydispersion degree (Mw/Mn): 1.1
Quantitation Data of Si—H group:
H (ppm): 101.6
from H (ppm): 9,843
Viscosity (25° C.): 165 centipoises

EXAMPLE 6

Preparation of dimethylsiloxane compound with a tridecafluoro-1,1,2,2-tetrahydrooctyl group at its α-position and a 3-aminopropyl group at its ω-position A 1-liter three-necked round flask with a stirrer and a cooler was charged with 98.4 g of the siloxane compound prepared in Reference Example 6 and 50 ml of toluene and heated to 110° C. After 5.2 ×10⁻⁴ g (1.0×10⁻⁶ mol) of chloroplatinic acid was added, 1.42 g (0.011 mol) of 3-(N-trimethylsilylamino)propene was added dropwise. After completion of dropwise addition, the mixture was maintained at the reaction temperature of 110° C. for 20 hours and then subjected to a reaction for removing a trimethylsilyl group using 100 g of methanol.

A low-boiling fraction of the reaction product was removed at 100° C./10 mmHg over a period of 2 hours and the object product was left as a still residue in a substantially quantitative yield.

The resulting siloxane compound was measured by IR spectrum, gel permeation chromatography (GPC) and viscosity, and the analysis results and amino group quantitation data are as shown below.

The resulting product was identified as having the following formula:

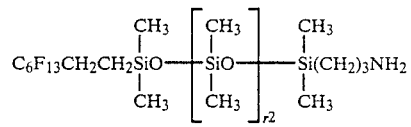

IR (KBr):
3400–3250cm⁻¹: (—NH₂)
2970cm⁻¹: (C—H)
1260cm⁻¹: (Si—CH₃)
1250-1150cm⁻¹: (CF₂, CF₃)
1120-1050cm⁻¹: (Si—O)
GPC (toluene), molecular weight converted into polystyrene
number-average molecular weight (Mn): 12,490
weight-average molecular weight (Mw): 13,410
polydispersion degree (Mw/Mn): 1.1
Quantitation Data of amino group:
amine equivalent 10,360
Viscosity (25° C.): 199 centipoises

REFERENCE EXAMPLE 7

Preparation of dimethylsiloxane compound (two siloxane chains based on the hydrosilyl group) with a tridecafluoro-1,1,2,2-tetrahydrooctyl group at its α- and α'-positions and a hydrosilyl group at its ω-position A 5-liter three-necked round flask with a stirrer and a cooler was charged with 1,000 ml of previously dried tetrahydrofuran, 50.0 g (0.119 mol) of (tridecafluoro1,1,2,2-tetrahydrooctyl)dimethylsilanol, and 1,130.2 g (5.08 mol) of hexamethylcyclotrisiloxane in a N₂ stream. After 0.40 ml of a hexane solution of butyl lithium (1.5 mol/liter) was added, the mixture was polymerized at 20° C. for 15 hours.

To this reaction mixture were added 7.51 g (0.0653 mol) of methyldichlorosilane and 14 g of triethylamine, and the resulting mixture was stirred for 1 hour to suspend the polymerization. The reaction mixture was then transferred to a separatory funnel and the salt produced was removed by washing with water. Thereafter, the reaction product was dried over anhydrous sodium sulfate.

A low-boiling fraction of the reaction product was removed at 100° C./10 mmHg over a period of 2 hours and the object product was left as a still residue in a substantially quantitative yield.

The resulting siloxane compound was measured by IR spectrum, gel permeation chromatography (GPC) and viscosity, and the analysis results and Si—H group quantitation data are as shown below. It is further found that, as the molecular weights calculated from the GPC data and H (ppm) were virtually twice those of Reference Example 6 (having one siloxane chain based on the hydrosilyl group) in which the conditions and scales were the same as in this reference example yet only the kind of chlorosilane added was changed, the reaction product has the following structure having two siloxane chains as reference to the hydrosilyl group.

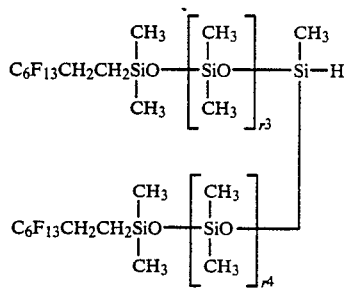

IR (KBr):
2970cm$^{-1}$: (C—H)
2250cm$^{-1}$: (Si—H)
1260cm$^{-1}$: (Si—CH$_3$)
1250–1150cm$^{-1}$: (CF$_2$, CF$_3$)
1120–1050cm$^{-1}$: (Si—O)
GPC (toluene), molecular weight converted into polystyrene
number-average molecular weight (Mn): 19,740
weight-average molecular weight (Mw): 23,720
polydispersion degree (Mw/Mn): 1.2
Quantitation Data of Si—H group:
H (ppm): 53.9
calculated molecular weight
from H (ppm): 18,550
Viscosity (25° C.): 423 centipoises

EXAMPLE 7

Preparation of dimethylsiloxane with tridecafluoro1,1,2,2-tetrahydrooctyl group at it α- and α'-positions and a 3-aminopropyl group at its ω-position A 1-liter three-necked round flask with a stirrer and a cooler was charged with 185.5 g of the siloxane compound prepared in Reference Example 7 and 100 ml of toluene and heated to 110° C. After 5.2 ×10 g (1.0×10$^{-6}$ mol) of chloroplatinic acid was added, 1.42 g (0.011 mol) of 3-(N-trimethylsilylamino)propene was added dropwise. After completion of dropwise addition, the mixture was maintained at the reaction temperature of 110° C. for 20 hours and then subjected to a reaction for removing a trimethylsilyl group using 300 g of methanol.

A low-boiling fraction of the reaction product was removed at 100° C./10 mmHg over a period of 2 hours and the object product was left as a still residue in a substantially quantitative yield.

The resulting siloxane compound was measured by IR spectrum, gel permeation chromatography (GPC) and viscosity, and the analysis results and amino group quantitation data are as shown below.

The resulting product was identified as having the following formula:

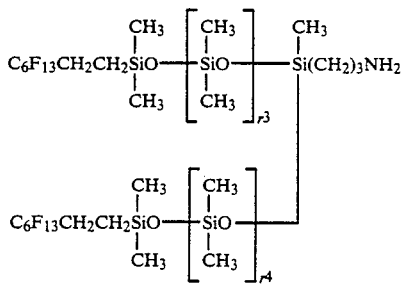

IR (KBr):
3400–3250cm$^{-1}$: (—NH$_2$)
2970cm$^{-1}$: (C—H)
1260cm$^{-1}$: (Si—CH$_3$)
1250–1150cm$^{-1}$: (CF$_2$, CF$_2$)
1120–1050cm$^{-1}$: (Si—O)
GPC (toluene), molecular weight converted into polystyrene
number-average molecular weight (Mn): 20,000
weight-average molecular weight (Mw): 23,920
polydispersion degree (Mw/Mn): 1.2
Quantitation Data of amino group:
amine equivalent: 19,140
Viscosity (25° C.): 483 centipoises

REFERENCE EXAMPLE 8

Preparation of dimethylsiloxane compound (three siloxane chains based on the hydrosilyl group)

with a tridecafluoro-1,1,2,2-tetrahydrooctyl group at its α-, α'- and α"-positions and a hydrosilyl group at its ω-position A 5-liter three-necked round flask with a stirrer and a cooler was charged with 1,000 ml of previously dried tetrahydrofuran, 50.0 g (0.119 mol) of (tridecafluoro1,1,2,2-tetrahydrooctyl)dimethylsilanol, and 1,130.2 g (5.08 mol) of hexamethylcyclotrisiloxane in a N$_2$ stream. After 0.40 ml of a hexane solution of butyl lithium (1.5 mol/liter) was added, the mixture was polymerized at 20° C. for 15 hours.

To this reaction mixture were added 5.90 g (0.0453 mol) of trichlorosilane and 14 g of triethylamine, and the resulting mixture was stirred for 1 hour to suspend the polymerization. The reaction mixture was then transferred to a separatory funnel and the salt Produced was removed by washing with water. Thereafter, the reaction product was dried over anhydrous sodium sulfate.

A low-boiling fraction of the reaction product was removed at 100° C./10 mmHg over a period of 2 hours and the object product was left as a still residue in a substantially quantitative yield.

The resulting siloxane compound was measured by IR spectrum, gel Permeation chromatography (GPC) and viscosity, and the analysis results and Si—H group quantitation data are as shown below. It is further found that, as the molecular weights calculated from the GPC data and H (pPm) were virtually three times those of Reference Example 6 (having one siloxane chain based on the hydrosilyl group) in which the conditions and scales were the same as in this reference example yet only the kind of the chlorosilan added was changed, the reaction product has the following structure having three siloxane chains as reference to the hydrosilyl group.

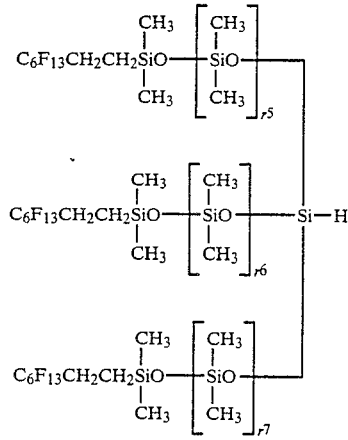

IR (KBr):
2970cm$^{-1}$: (C—H)
2250cm$^{-1}$: (Si—H)
1260cm$^{-1}$: (Si—CH$_3$)
1250–1150cm$^{-1}$: (CF$_2$, CF$_3$)
1120–1050cm$^{-1}$: (Si—O)
GPC (toluene), molecular weight converted into polystyrene
number-average molecular weight (Mn): 33,790
weight-average molecular weight (Mw): 37,710
polydispersion degree (Mw/Mn): 1.1
Quantitation Data of Si—H group:
H (ppm): 33.8
calculated molecular weight
from H (ppm): 29,590
Viscosity (25° C.): 681 centipoises

EXAMPLE 8

Preparation of dimethylsiloxane compound with a tridecafluoro-1,1,2,2-tetrahydrooctyl group at its α-, α'- and α''-positions and a 3-aminopropyl group at its ω-position A 1-liter three-necked round flask with a stirrer and a cooler was charged with 295.9 g of the siloxane compound prepared in Reference Example 8 and 100 ml of toluene and heated to 110° C. After 5.2 ×10$^{-4}$ g (1.0×10$^{-6}$ mol) of chloroplatinic acid was added, 1.42 g (0.011 mol) of 3-(N-trimethylsilylamino)propene was added dropwise. After completion of dropwise addition, the mixture was maintained at the reaction temperature of 110 for hours and then subjected to a reaction for removing a trimethylsilyl group using 300 g of methanol.

A low-boiling fraction of the reaction product was removed at 100° C./10 mmHg over a period of 2 hours and the object product was left as a still residue in a substantially quantitative yield.

The resulting siloxane compound was measured by IR spectrum, gel permeation chromatography (GPC) and viscosity, and the analysis results and hydroxy group quantitation data are as shown below.

The resulting product was identified as having the following formula:

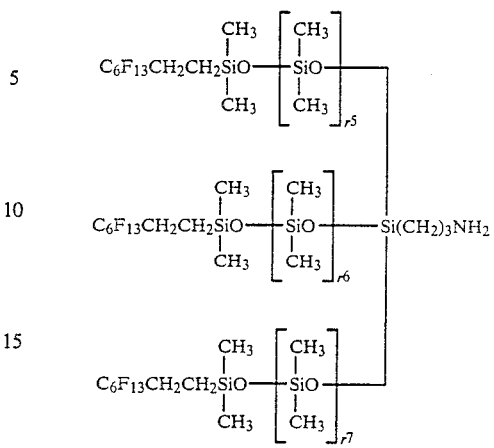

IR (KBr):
3400–3250cm$^{-1}$: (—NH$_2$)
2970cm$^{-1}$: (C—H)
1260cm$^{-1}$: (Si—CH$_3$)
1250–1150cm$^{-1}$: (CF$_2$, CF$_3$)
1120–1050cm$^{-1}$: (Si—O)
GPC (toluene), molecular weight converted into polystyrene
number-average molecular weight (Mn): 33,480
weight-average molecular weight (Mw): 40,230
polydispersion degree (Mw/Mn): 1.2
Quantitation Data of amino group:
amine equivalent: 29,780
Viscosity (25° C.): 675 centipoises The polyorganosiloxane compounds according to the Present invention are novel compounds having a fluorine-containing substituent at an α-position and an amino group at an ω-position, having a fluorine-containing substituent at least at either an α- or α'-position and an amino group at an ω-position, or having a fluorine-containing substituent at least at either an α-, α'- or α''-position and an amino group at an ω-position. The polyorganosiloxane compounds may provide the following advantages when they are chemically incorporated into a synthetic resin having reactive groups, such as polyamides, polyimides, polyurethane, epoxy resins or synthetic resins having a substituent reactive with the amino group.

(1) As the reactive group or groups of the polyorganosilane compound is or are chemically bonded to the synthetic resin such as polyamides, polyimides, polyurethane, epoxy resins or other synthetic resins having a group reactive with the amino group, a reduction in desirable characteristics can be prevented even with the passage of time.

(2) As the fluoroalkyl group resides in the same molecule, the polyorganosiloxane compounds according to the present invention provide the synthetic resins with various characteristics such as repellency against water, oil or snow, an anti-fouling property, mold releasability, non-adhesion, and low friction properties, which conventional polysiloxane compounds with a trimethylsiloxy group at its terminal cannot provide, or better than those conventional polysiloxane compounds can provide, without impairing the various functions of the polyorganosiloxane compounds.

(3) As the preferred polyorganosiloxane compounds according to the present invention has a distribution of molecular weights within a range as narrow as from 1.1 to 1.2, their molecular chains are said to be relatively equal in length so that the synthetic resin into which such a polyorganosiloxane compound is introduced can provide a modified resin with a more uniform structure than a polysiloxane compound having molecular chains having different length. In addition, the polyorganosiloxane compounds cause no production of a cyclic dimethylsiloxane that cannot be removed, which could not be avoided by the equilibrium reaction by means of a conventional acidic or basic catalyst, thereby preventing a reduction of desirable characteristics, bleeding and a fluctuation in quality between products on account of the cyclic by-product and improving the properties of the resulting products.

(4) In using the polyorganosiloxane compounds according to the present invention as a graft polymer for improvements in various functions and characteristics of the synthetic resin, such as water and oil repellency, anti-fouling properties, mold releasability, non-adhesion and low frictional properties, they can provide the synthetic resin with the properties of the siloxane compound and, in addition thereto, with the peculiar functions inherent in the fluoroalkyl group thereof. The polyorganosiloxane compound enables the provision of the synthetic resin with a relatively uniform structure and, furthermore, a control over the characteristics of the resulting synthetic resin by changing the length of molecular chains of the siloxane moiety and the fluoroalkyl moiety in accordance with usage. Thus, as compared with conventional dimethylsiloxane compounds of the type having no fluoroalkyl group, the polyorganosiloxane compounds permit a wide application of the synthetic resins to usage requiring high performance, particularly surface modification. Such characteristics can be realized by the polyorganosiloxane compound in a lesser amount than the conventional siloxane compound so that an adverse influence of the siloxane upon the basic properties of the synthetic resin can be blocked to a maximum extent.

(5) As the number of siloxane chains of the polyorganosiloxane compound on the basis of the hydrosilyl group reactive with the synthetic resin can be selected arbitrarily from one to three, as the length of the siloxane chains can be changed, and as the kind of fluorine-containing group residing in the siloxane chain at its terminal can be determined, in accordance with the present invention, the properties of molded products formed from the polyorganosiloxane compounds of the present invention and a synthetic resin can be provided by suitable selection of the polyorganosiloxane compounds.

It is to be understood that the present invention may be embodied in other specific forms without departing from the spirit and scope thereof. The present embodiments are therefore to be considered in all respects as illustrative and not restrictive, the scope of the invention being indicated by the appended claims, and all the changes, modifications and variations which come within the meaning and range of equivalency of the claims are therefore intended to be encompassed within the spirit and scope of the invention.

What is claimed is:

1. A polyorganosiloxane compound represented by the following general formula (I):

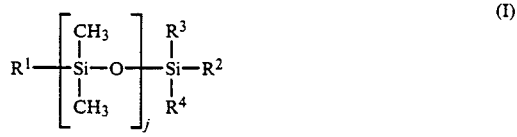

in which
j is an integer from 2 to 2,000;
$R^1$ is a pentafluorophenyl group or a linear or branched fluoroalkyl group as represented by the following general formula (II):

$$C_aH_bF_{2a-b+1} \quad (II)$$

(wherein a is an integer from 3 to 18 and b is 0 or 2a;
$R^2$ is a substituent as represented by formula (III):

$$-CH_2CH_2CH_2NH_2 \quad (III)$$

; and
$R^3$ and $R^4$ are independently each an alkyl group having from 1 to 4 carbon atoms or a phenyl group.

2. A polyorganosiloxane compound as claimed in claim 1, wherein the substituent represented by the symbol $R^1$ is 3,3,3-trifluoropropyl group, tridecafluoro-1,1,2,2-tetrahydrooctyl group or heptadecafluoro-1,1,2,2-tetrahydrodecyl group.

3. A polyorganosiloxane compound as claimed in claim wherein the substituent $R^3$ and $R^4$ are independently each methyl group.

4. A polyorganosiloxane compound as represented by the following general formula (IV):

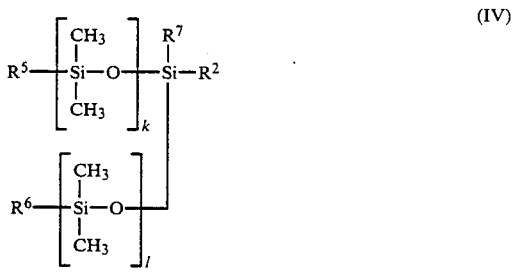

in which
k and l are independently each an integer from 2 to 2,000;
$R^5$ and $R^6$ are independently each an alkyl group having from 1 to 4 carbon atoms, pentafluorophenyl group or a linear or branched fluoroalkyl group as represented by the following general formula (II):

$$C_{al\ Hb}F_{2a-b+1} \quad (II)$$

wherein a is an integer from 3 to 18 and b is 0 or 2a, provided, however, that at least one of $R^5$ and $R^6$ is the pentafluorophenyl group or the fluroalkyl group;
$R^2$ is an substituent as represented by formula (III):

$$-CH_2CH_2CH_2NH_2 \quad (III)$$

; and $R^7$ is an alkyl group having 1 to 4 carbon atoms or a phenyl group.

5. A polyorganosiloxane compound as claimed in claim 4, wherein the substituents represented by the symbols $R^5$ and $R^6$ in the general formula (IV) are independently each an alkyl group having 1 to 4 carbon atoms, 3,3,3-trifluoropropylgroup, tridecafluoro-1,1,2,2-tetrahydrooctyl group or heptadecafluoro-1,1,2,2-tetrahydrodecyl group provided, however, that at least one of $R^5$ and $R^6$ is the fluoro-containing group.

6. A polyorganosiloxane compound as claimed in claim 4, wherein the substituents represented by the symbols $R^5$ and $R^6$ in the general formula (IV) are independently each 3,3,3-trifluoropropylgroup, tridecafluoro-1,1,2,2-tetraoctyl group or heptadecafluoro-1,1,2,2-tetrahydrodecyl group.

7. A polyorganosiloxane compound as claimed in claim 4, wherein the symbol $R^7$ in the general formula (IV) is methyl.

8. A polyorganosiloxane compound as represented by the following general formula (V):

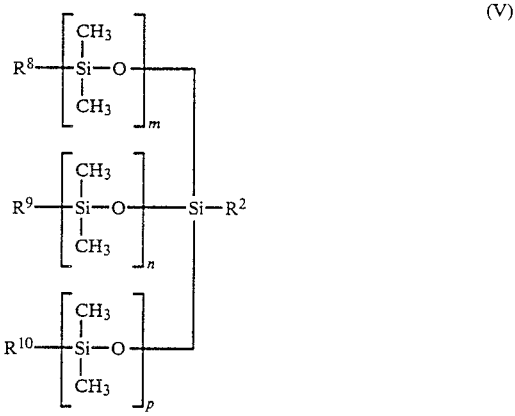

in which
m, n and p are independently each an integer from 2 to 2,000;
$R^8$, $R^9$ and $R^{10}$ are independently each an alkyl group having from 1 to 4 carbon atoms, pentafluorophenyl group or a linear or branched fluoroalkyl group as represented by the following general formula (II):

$$C_aH_bF_{2a-b+1} \qquad (II)$$

(wherein a is an integer from 3 to 18 and b is 0 or 2a,
provided, however, that at least one of $R^6$, $R^9$ and $R^{10}$ is the pentafluorophenyl group or the fluroalkyl group; and
$R^2$ is a substituent as represented by formula (III):

$$-CH_2CH_2CH_2HN_2 \qquad (III)$$

9. A polyorganosiloxane compound as claimed in claim 8, wherein the substituents as represented by the reference symbols $R^8$, $R^9$ and $R^{10}$ of the general formula (V) are independently each an alkyl group having from 1 to 4 carbon atoms, 3,3,3-trifluoropropyl, tridecafluoro1,1,2,2-tetrahydrooctyl group or heptadecafluoro-1,1,2,2tetrahydrodecyl group and at least one of $R^8$, $R^9$ and $R^{10}$ is the fluorine-containing substituent selected from the above substituents.

10. A polyorganosiloxane compound as claimed in claim 8, wherein the substituents as represented by the reference symbol $R^8$, $R^9$ and $R^{10}$ are each 3,3,3-trifluoropropyl, tridecafluoro-1,1,2,2-tetrahydrooctyl group or heptadecafluoro-1,1,2,2- tetrahydrodecyl group.

* * * * *

UNITED STATES PATENT AND TRADEMARK OFFICE
CERTIFICATE OF CORRECTION

PATENT NO. : 4,996,280

DATED : February 26, 1991

INVENTOR(S) : Saho et al.

It is certified that error appears in the above-identified patent and that said Letters Patent is hereby corrected as shown below:

Claim 1, column 26, line 18, delete "(" before "wherein".

Claim 8, column 28, line 30, delete "(" before "wherein"; line 32, change "$R^6$" to --$R^8$--.

Claim 9, column 28, lines 44 and 45, change "heptadecafluoro-1,1,2,2tetrahydrodecyl" to --heptadecafluoro-1,1,2,2-tetrahydrodecyl--.

Signed and Sealed this

First Day of September, 1992

Attest:

DOUGLAS B. COMER

Attesting Officer

Acting Commissioner of Patents and Trademarks